United States Patent [19]

Narayan et al.

[11] Patent Number: 4,717,774

[45] Date of Patent: Jan. 5, 1988

[54] PROCESS FOR THE PREPARATION OF TOLUENE DIAMINES

[75] Inventors: Thirumurti Narayan, Grosse Ile; Peter T. Kan, Plymouth, both of Mich.

[73] Assignee: BASF Corporation, Parsippany, N.J.

[21] Appl. No.: 811,480

[22] Filed: Dec. 20, 1985

[51] Int. Cl.[4] .............................................. C07C 51/16
[52] U.S. Cl. .................................................. 564/422
[58] Field of Search .......................................... 564/422

[56] References Cited

U.S. PATENT DOCUMENTS

| 1,124,776 | 1/1915 | Marwedel | 564/422 |
| 3,517,063 | 6/1970 | Nason | 564/422 |
| 3,637,820 | 1/1972 | Dodman et al. | 564/422 X |
| 3,801,640 | 4/1974 | Knifton | 564/422 X |
| 3,935,264 | 1/1976 | Bhutani | 564/422 |

Primary Examiner—Paul F. Shaver
Attorney, Agent, or Firm—John C. Demeter; D. B. McKenzie-Wardell; Joseph D. Michaels

[57] ABSTRACT

The invention relates to an improved process for the preparation of toluene diamine from dinitrotoluene involving hydrogenation of dinitrotoluene with hydrogen gas at elevated temperatures and super atmospheric pressure in the presence of a supported nickel catalyst and carbon monoxide ranging from 0.001 to 0.1 volume percent. The rate of hydrogenation, product quality and yield are improved when hydrogen spiked with small amounts of carbon monoxide was used.

4 Claims, No Drawings

PROCESS FOR THE PREPARATION OF TOLUENE DIAMINES

BACKGROUND OF THE INVENTION

1. Field of the Invention

This invention relates to a process for the preparation of toluene diamine from dinitrotoluene. More specifically, the invention relates to the hydrogenation of the dinitrotoluene at elevated temperatures and super atmospheric pressure in the presence of a supported nickel catalyst with hydrogen gas spiked with carbon monoxide. The amount of carbon monoxide used to spike the hydrogen is a small amount ranging from 0.001 to 0.2 volume percent based on the total amount of hydrogen.

2. Description of the Prior Art

The prior art, as evidenced by U.S. Pat. Nos. 4,387,247; 4,535,162; 3,637,820; and 3,925,264, discloses various methods of reducing the nitroaromatic compounds by hydrogen.

U.S. Pat. No. 4,387,247 teaches the reduction of di- or polynitroaromatic compounds by gaseous hydrogen sulfide over solid catalyst. The carbon monoxide gas is added to promote formation of the amino groups from the nitro groups. The carbon monoxide is added in sufficient amounts to obtain reduction of two or more nitro groups to afford di- or polyamines as the major reaction products. The purpose of the carbon monoxide is to prolong the life of the catalyst for reduction of at least two nitro groups in the aromatic compound to amino groups.

U.S. Pat No. 3,637,820 discloses a process for the manufacture of aromatic primary amines by reacting in the presence of a catalyst, an aromatic nitro compound, and a reducing agent. The reducing agent taught in this patent is selected from the group consisting of hydrogen and carbon monoxide and water or aliphatic alcohol. The catalyst consists of two or three heavy metals selected from the group consisting of magnesium, iron, cobalt, nickel, copper, silver and cerium as their oxides, hydroxides or carbonates. This invention teaches the reduction of aromatic nitro compounds to primary amines at relatively low temperatures and pressures utilizing as catalysts certain compositions comprising oxygenated compounds of at least two heavy metals. The reducing agent taught comprises hydrogen or carbon monoxide and water or aliphatic alcohol in the presence of the catalyst comprising two or more heavy metals.

U.S. Pat. No. 4,535,162 discloses a process for catalytically reducing nitroaromatic compounds by displacement of hydrogen from carbon monoxide and water or from synthesis gas to nitroaromatic compounds. The catalytic reduction utilizes complexes of rhodium, iridium, ruthenium and osmium in the presence of or containing bidentate or tridentate nitrogen aromatic chelates. The catalytic activity is higher than the hydrogen displacement catalyst. The process is carried out in a carbon monoxide/water system or a carbon monoxide/hydrogen plus water system. The products obtained from the hydrogenation of the starting nitroaromatic compounds consist of aryl amines and are utilized as intermediates for organic syntheses. The catalytic system disclosed in this invention comprises complexes of rhodium, iridium, ruthenium and osmium.

U.S. Pat. No. 3,935,264 teaches hydrogenation of dinitrotoluene to toluene diamine in the presence of an aliphatic alcohol solvent. A small amount of carbon monoxide is added to the aliphatic alcohol solvent to improve the hydrogenation reaction. The teachings disclosed apply to any process where dinitrotoluene is hydrogenated in the presence of an aliphatic alcohol to the corresponding toluene diamine and wherein an alkyl toluene diamine is formed as a by-product. The aliphatic alcohol serves as a reaction solvent medium. The patent teaches that in the absence of an aliphatic alcohol solvent the hydrogenation reaction is reduced or the efficiency of the reaction adversely affected. The hydrogenation catalyst disclosed in this patent are metallic catalysts including mixtures thereof and may be supported on a carrier or not. The proportion of carbon monoxide taught in the patent is from 0.05 to about 20 percent by volume based on the volume of the hydrogen utilized, preferably from 0.3 to 6 percent by volume.

The prior art has not taught the preparation of toluene diamine from dinitrotoluene utilizing a hydrogen system, a metallic catalyst and a small amount of carbon monoxide, specifically from 0.001 to 0.2 volume percent.

SUMMARY OF THE INVENTION

It has been unexpectedly discovered that the rate of hydrogenation, product quality and yield improved when hydrogen spiked with small amounts of carbon monoxide was used. The invention relates to an improved process for the preparation of toluene diamine from dinitrotoluene involving hydrogenation of dinitrotoluene with hydrogen gas at elevated temperatures and super atmospheric pressure in the presence of a supported nickel catalyst and carbon monoxide ranging from 0.001 to 0.2 volume percent based on the total amount of hydrogen.

DESCRIPTION OF THE PREFERRED EMBODIMENT

In accordance with the subject invention, toluene diamine is prepared from dinitrotoluene by a hydrogenation process with hydrogen gas at elevated temperatures and super atmospheric pressure in the presence of a supported nickel catalyst and a small amount of carbon monoxide.

The improvement disclosed herein applies to any process wherein a dinitrotoluene is hydrogenated to the corresponding toluene diamine. Thus, the dinitrotoluene can be an isomer of this compound or a mixture of isomers. Illustrative are 2,3-dinitrotoluene, 2,4-dinitrotoluene, 2,5-dinitrotoluene, 2,6-dinitrotoluene, 3,4-dinitrotoluene and 3,5-dinitrotoluene and mixtures thereof. However, it is preferred to employ a nonvicinal isomer or mixtures of such isomers, such as 2,4-dinitrotoluene, 2,5-dinitrotoluene, 2,6-dinitrotoluene and 3,5-dinitrotoluene. The most preferred dinitrotoluene isomers are 2,4-dinitrotoluene, 2,6-dinitrotoluene and mixtures thereof.

In carrying out the hydrogenation reaction, any aliphatic alcohol, water, or a mixture thereof may be employed to serve as a reaction solvent medium without adversely interferring with the hydrogenation reaction or the products. Usually the substituted alkyl monoalcohols are employed which contain from 1 to 8, and preferably 1 to 4 carbon atoms. Illustrative are methanol, ethanol, isopropanol, butanol, pentanol, and mixtures thereof. The most preferred solvent is water. Widely varying amounts of solvent may be used in carrying out the hydrogenation reaction. Any suitable portion of solvent may be employed such as from 10 to 100 and preferably about 15 to 60 parts per 100 parts by weight of the dinitrotoluene.

Hydrogenation reaction is preferably carried out in the presence of a hydrogenation catalyst. Any variety of catalyst which has been disclosed in the prior art for promoting this type of reaction may be employed. It is generally preferred to employ a metallic catalyst including mixtures comprising such catalyst. Furthermore common catalyst may be either supported on a carrier or unsupported. A particularly preferred group of catalysts is comprised of nickel, cobalt, magnesium, copper, silver, and mixtures thereof; and in accordance with the most preferred embodiment of the invention, a catalyst comprised of supported nickel is employed. The proportion of hydrogenation catalyst may be varied over a wide range, as any suitable proportion which is effective in catalyzing the hydrogenation reaction may be employed. Usually catalytic proportions are employed such as from about 1 to 10 percent, and preferably about 2 to 5 percent, by weight of the dinitrotoluene.

In accordance with the invention, the hydrogenation of dinitrotoluene is carried out in the presence of carbon monoxide gas. This gas may be fed into the reaction zone as a separate stream or as a component of the hydrogen stream. The later practice is preferred, the carbon monoxide being sprayed into the hydrogen stream before its introduction into the reaction zone. It is preferred to spike the hydrogen stream before introduction into the reaction zone. Following the teachings of this invention, it is significant to note that the carbon monoxide is used in relatively small proportions so that the formation of the toluene diamine is effected primarily via the hydrogenation of dinitrotoluene. This is important for two reasons. One is that using proportions of carbon monoxide greater than 0.2 percent results in contamination or poisoning of the hydrogenation catalyst, thereby reducing its effectiveness. Secondly, hydrogen is generally more effective than carbon monoxide in bringing about the reduction of dinitrotoluene. The proportion of carbon monoxide which is used according to the invention may be varied from about 0.001 to 0.2 percent by volume based on the volume of hydrogen that is employed. However, pursuant to the preferred embodiment and the invention, a carbon monoxide proportion is used which varies from 0.001 to 0.2 and still more preferably about 0.001 to 0.15 percent by volume based on the volume of hydrogen.

In carrying out the hydrogenation dinitrotoluene usually a sufficient proportion or pressure of hydrogen is used, preferably a proportion so as to saturate the reactor contents with hydrogen. In practice, the reactor is supplied with hydrogen at a pressure from about 200 psi to 1000 psi and preferably about 200 psi to 500 psi. The hydrogenation reaction is carried out at an elevated temperature. Preferred is a temperature from about 80° C. to 200° C. and more preferably from 90° to 140° C.

Any suitable procedure may be employed in practicing the process of the invention. For example, a mixture of dinitrotoluene, solvent and catalyst is fed to a reactor which is equipped with a mechanical agitator and a thermometer. Conventional means are provided for controlling the temperature inside the reactor. Hydrogen and carbon monoxide supplied in separate streams or as a single stream are fed to the reactor preferably by one or more inlets located below the surface of the dinitrotoluene solvent mixture and the hydrogen pressure is regulated to a desired level. The agitator mixture is heated to the desired temperature and maintained at that temperature until the reaction is completed. A liquid reaction product mixture, consisting mostly of toluene diamine, solvent, and catalyst is thus obtained. The toluene diamine is then recovered from this mixture by filtering off the catalyst and distilling off the solvent. The process described herein may be carried out on a continuous basis.

The improved hydrogenation process of the invention provides a simple and economical method for preparing toluene diamine with improved product quality and yield. Furthermore, this result is achieved with an increase in the rate of hydrogenation without adverse effect on product yield and quality. The toluene diamine thus obtained can be used directly without further purification in the preparation of toluene diisocyanate which can be used in the preparation of polyurethane elastomers and foam.

To best illustrate the aspect of the invention involving the unexpected improved rate of hydrogenation, product quality and yield obtained when hydrogen spiked with 0.001 to 0.2 volume percent of carbon monoxide was used for the hydrogenation, comparative data has been tabulated. Accordingly, the following is the discussion of the experimental methods and the comparative results obtained.

The following is a list of abbreviations used in Table I.

DNT—dinitrotoluene
TDA—toluenediamine
$H_2$—hydrogen gas
CO—carbon monoxide
Ni catalyst—Nickel hydrogenation catalyst containing 60 to 70 percent nickel on clay support; percent by weight of DNT.
ANT—aminonitrotoluene, partially reduced nitro impurity.

General Method Used for the Laboratory Hydrogenation of Dinitrotoluene

Hydrogenations were run on a semi-continuous basis in a one-gallon autoclave. The autoclave was equipped with PULSAFEEDER diaphragm pump to deliver a known amount of dinitrotoluene an outlet for venting gas, gas inlet, a dip tube for recycle, thermowell, DISPERSIMATIC type agitator and a discharge tube at the bottom of the clave. The autoclave was charged with a "heel" composition consisting of toluenediamine in water.

Desired amount of dry nickel catalyst was added to this charge, purged with nitrogen gas and thereafter pressurized with hydrogen gas to 200 to 500 psig, heated with agitation at 80° to 150° C. and held at that temperature for one-half hour to reduce the catalyst to the active form. Thereafter, molten dinitrotoluene was pumped into the autoclave at a predetermined rate per minute and the hydrogen line was opened up to a hydrogen supply at 200 to 500 psig. A slight exotherm usually occurred at this point and the reaction conditions of temperature and pressure were maintained until the hydrogen uptake was completed as indicated by a rotameter in the hydrogen supply line.

After dinitrotoluene addition and the hydrogen uptake was completed, the contents were allowed to stir for ten minutes. Then the autoclave contents were cooled to room temperature, the stirrer was shut off and the product was discharged using the bottom discharge tube. In the multicycle hydrogenations, after cooling the autoclave contents to room temperature, the stirrer was shut off, the crude product was allowed to stand for two hours to allow the catalyst to settle to the bottom. About 60 percent of the crude product was then removed off the top by pressurizing with a few pounds of hydrogen and blowing the product out through the dip tube. The catalyst and a portion of the crude product (approximately the same amount of the initial heel) remained in the autoclave. After the step, the autoclave was pressurized to the required pressure with hydrogen gas heated to the desired temperature, and new dinitrotoluene was pumped into the autoclave at the desired rate.

The above procedure of hydrogenation, catalyst settling and product discharge was repeated after the completion of each cycle. After the final hydrogenation cycle, the total crude toluenediamine product was discharged from the autoclave through the bottom discharge valve. The crude toluenediamine product obtained in the final hydrogenation cycle of all the runs was filtered using a preformed bed of dry CELITE on a coarse filter paper supported by a coarse fritted-glass funnel to remove as much of the nickel catalyst as possible.

Work-up of the Crude Toluenediamine Product

About 150 g of the crude toluenediamine product was weighed into a 300 ml distillation flask with ethanol and water or water and were distilled at atmospheric pressure (no column) using a silicone 200 fluid bath until the pot temperature reached 140° C. Thereafter, the distillation head was removed, and the flask was attached with a 6" Vigereux column and a take-off. The column and the take-off were wrapped with a heating tape to keep the distilling toluenediamine molten. Toluene diamine was then distilled under reduced pressure until the bath temperature reached 170° C. (0.2 mm of mercury) and held under these conditions until all the toluenediamine distilled over. High boiling residue and tar remained in the flask. The distillation and the toluenediamine receiver were then weighed and The toluenediamine yield was calculated.

Comparative Data

In interpreting the data, the rate of hydrogenation was judged on the basis of hydrogen fall-off time and the amount of the starting material present the instant after the hydrogenation was completed. The hydrogen fall-off time is best described as the time period in which demand for hydrogen continues after the addition of dinitrotoluene has been completed. The most efficient hydrogenation will, therefore, be indicated by the completion of the dinitrotoluene addition and hydrogen demand. Therefore, the shorter the hydrogen fall-off time, the better the hydrogenation rate.

Table I summarizes the data of hydrogenations using water as the solvent. The data indicates improved hydrogenation rate and product quality with carbon monoxide spiked hydrogen. Illustrated is the increased rate of hydrogenation and improved product quality and yield when hydrogen gas is spiked with small amounts of carbon monoxide. Reduced amounts of unreduced dinitrotoluene and partially reduced aminonitrotoluene are found in the TDA indicating improved quality. No other impurities such as alkylaminotoluenes are found in the product.

TABLE I

| Feed | Heel | | Conditions | |
|---|---|---|---|---|
| DNT: 910.6 g | TDA: | 488 g | Temperature: | 80–150° C. |
| | Water: | 288 g | Pressure: | 150–500 psig |
| | Catalyst: | 3–7% 7% wt. DNT | | |

| Experiment No. | Hydrogenation Cycle | CO in H$_2$, Volume % | Fall-off Time sec. | TDA Yield % | Crude TDA Analysis, PPM | |
|---|---|---|---|---|---|---|
| | | | | | DNT | ANT |
| 1 | Initial run | None | 25 | 98.0 | 830 | 692 |
| 2 | 1st recycle | None | 25 | 98.7 | | |
| 3 | 2nd recycle | None | 35 | 98.8 | | |
| 4 | 3rd recycle | None | 40 | 98.9 | 29 | 6 |
| 5 | Initial run | 0.0010 | 30 | 98.0 | 1122 | 569 |
| 6 | 1st recycle | 0.0010 | 30 | 98.2 | | |
| 7 | 2nd recycle | 0.0010 | 29 | 98.3 | | |
| 8 | 3rd recycle | 0.0010 | 30 | 96.9 | 21 | 65 |
| 9 | Initial run | 0.0102 | 30 | 98.6 | 1318 | 755 |
| 10 | 1st recycle | 0.0102 | 30 | 98.0 | | |
| 11 | 2nd recycle | 0.0102 | 30 | 98.5 | | |
| 12 | 3rd recycle | 0.0102 | 30 | 98.7 | None | None |
| 13 | Initial run | 0.100 | 25 | 97.8 | 5 | 91 |
| 14 | 1st recycle | 0.100 | 30 | 97.9 | | |
| 15 | 2nd recycle | 0.100 | 30 | 98.0 | | |
| 16 | 3rd recycle | 0.100 | 30 | 98.4 | None | None |

The embodiments of the invention in which an exclusive property or privilege is claimed are defined as follows:

1. A process of preparing toluene diamine consisting essentially of reacting dinitrotoluene with hydrogen in the presence of
    (a) water,
    (b) a metallic catalyst wherein the metal is nickel, cobalt, magnesium, copper or silver, and
    (c) carbon monoxide wherein the amount of carbon monoxide used is from 0.001 to 0.2 percent by volume based on the volume of hydrogen.

2. The process of claim 1 wherein said catalyst is supported nickel.

3. The process of claim 1 wherein a reaction temperature of 80° C. to 200° C. is employed.

4. The process of claim 1 wherein said hydrogen is supplied at a pressure of 200 to 450 psig.

* * * * *